(12) United States Patent
Fairless et al.

(10) Patent No.: US 12,176,097 B2
(45) Date of Patent: Dec. 24, 2024

(54) METHODS FOR MANAGING HEALTH CARE INFORMATION

(71) Applicant: ScriptLock, Canton, OH (US)

(72) Inventors: Brandon Fairless, Avon Lake, OH (US); Christopher Cutter, Canton, OH (US); Zachary Linquist, Canton, OH (US); Daniel Capri, North Canton, OH (US); Jon Bishop, North Canton, OH (US)

(73) Assignee: SCRIPTLOCK, Canton, OH (US)

( * ) Notice: Subject to any disclaimer, the term of this patent is extended or adjusted under 35 U.S.C. 154(b) by 729 days.

(21) Appl. No.: 17/196,319

(22) Filed: Mar. 9, 2021

(65) Prior Publication Data

US 2021/0280306 A1   Sep. 9, 2021

Related U.S. Application Data

(60) Provisional application No. 62/987,277, filed on Mar. 9, 2020.

(51) Int. Cl.
*G16H 40/20* (2018.01)
*G06F 9/54* (2006.01)
(Continued)

(52) U.S. Cl.
CPC ............ *G16H 40/20* (2018.01); *G06F 9/547* (2013.01); *G06F 16/2379* (2019.01);
(Continued)

(58) Field of Classification Search
CPC ........ G16H 40/20; G16H 10/60; G16H 15/00; G06F 9/547; G06F 16/2379; G06F 16/27;
(Continued)

(56) References Cited

U.S. PATENT DOCUMENTS 10,720,232 B2  7/2020 Giordano et al.
11,531,975 B2 * 12/2022 Verma ................ G06Q 20/0655
(Continued)

FOREIGN PATENT DOCUMENTS

CN   109242681 B  * 11/2020  ............. G06Q 40/04

OTHER PUBLICATIONS

Bazzoli, Fred. "ONC seeks proposals for using blockchain in healthcare; ONC seeks proposals for using blockchain in healthcare." Health Data Management (web content). Jul. 12, 2016 (Year: 2016).*

*Primary Examiner* — Linh Giang Le
(74) *Attorney, Agent, or Firm* — Wentsler LLC

(57) ABSTRACT

A computer-implemented method utilizing blockchain technology for managing healthcare records is provided. The computer-implemented method comprises providing a computer network with one or more computing devices that are interconnected through the computer network. The computer-implemented method comprises submitting a proposal from a first computing device of the one or more computing devices to a plurality of endorsing peers for approval. The computer-implemented method comprises approving the proposal by the plurality of endorsing peers with the at least one computing device and replying to the proposal with a response comprising a peer approved transaction. The computer-implemented method comprises creating a private peer-to-peer communication channel between the first computing device and a second computing device. The computer-implemented method comprises creating a block of transactions and adding the block of transactions to a ledger.

17 Claims, 3 Drawing Sheets

(51) Int. Cl.
*G06F 16/23* (2019.01)
*G06F 16/27* (2019.01)
*G06F 21/62* (2013.01)
*G16H 10/60* (2018.01)
*H04L 9/32* (2006.01)
*H04L 67/104* (2022.01)
*H04L 67/141* (2022.01)
*H04L 9/00* (2022.01)

(52) U.S. Cl.
CPC .......... *G06F 16/27* (2019.01); *G06F 21/6245* (2013.01); *G16H 10/60* (2018.01); *H04L 9/3239* (2013.01); *H04L 67/104* (2013.01); *H04L 67/141* (2013.01); *H04L 9/50* (2022.05)

(58) Field of Classification Search
CPC ... G06F 21/6245; G06F 21/64; H04L 9/3239; H04L 67/104; H04L 67/141; H04L 9/50; H04L 9/3263; H04L 67/12
See application file for complete search history.

(56) References Cited

U.S. PATENT DOCUMENTS

| 2018/0060496 A1* | 3/2018 | Bulleit | H04L 9/0643 |
| 2019/0149633 A1* | 5/2019 | Evans | G06F 21/6245 |
| | | | 709/217 |

* cited by examiner

METHODS FOR MANAGING HEALTH CARE INFORMATION

CROSS-REFERENCE TO RELATED APPLICATIONS

The following application claims the benefit of priority to U.S. Provisional Application No. 62/987,277, titled "METHODS FOR RECORDING AND ANALYZING MEDICAL REQUEST TRANSACTIONS" and filed on Mar. 9, 2020. The application is herein incorporated by reference.

FIELD

The present disclosure relates generally to methods for managing healthcare records and, more particularly, to methods for managing healthcare records by using blockchain technology.

BACKGROUND

It is generally known to manage healthcare records. In addition, storing medical records can be done using an electronic medical record system. However, problems related to the safe storage and transmission of data between multiple parties may occur. In addition, due to the different software systems utilized by the multiple parties, inefficiencies related to the transmission of data between the multiple parties may occur, thus increasing costs and down-time.

SUMMARY

The following presents a simplified summary of the disclosure to provide a basic understanding of some embodiments described in the detailed description.

In some embodiments, a computer-implemented method utilizing blockchain technology for managing healthcare records is provided. The computer-implemented method comprises providing a computer network with one or more computing devices that are interconnected through the computer network. The computer-implemented method comprises submitting a proposal related to a healthcare record from a first computing device of the one or more computing devices to a plurality of endorsing peers for approval, each of the endorsing peers comprising at least one computing device. The computer-implemented method comprises approving the proposal by the plurality of endorsing peers with the at least one computing device and replying to the proposal with a response comprising a peer approved transaction. The computer-implemented method comprises approving the proposal by the plurality of endorsing peers with the at least one computing device and replying to the proposal with a response comprising a peer approved transaction. The computer-implemented method comprises creating a private peer-to-peer communication channel between the first computing device and a second computing device and transmitting data related to the healthcare record from the first computing device to the second computing device through the private peer-to-peer communication channel. The computer-implemented method comprises creating a block of transactions based on the data transmitted from the first computing device to the second computing device and adding the block of transactions to a ledger.

In some embodiments, wherein the creating the private peer-to-peer communication channel between the first computing device and the second computing device comprises storing the data in a private state database on peers of authorized organizations and the data is accessible in the private state database from a chaincode.

In some embodiments, the creating the block of transactions comprises creating a hash value of the data and writing the hash value on a ledger of each of the peers of authorized organizations, wherein the ledger stores entries of the healthcare records that are invoked by the one or more computing devices.

In some embodiments, the ledger comprises a first smart contract that is assigned to a first peer on the first computing device and a second smart contract that is assigned to a second peer on the second computing device.

In some embodiments, the private peer-to-peer communication channel is created after one or more of the first smart contract or the second smart contract are approved by the plurality of endorsing peers.

In some embodiments, creating the private peer-to-peer communication channel comprises using a communication channel to exchange information to allow a connection over a secured API to be formed to exchange the data.

In some embodiments, a computing system utilizing blockchain technology for managing healthcare records is provided. The computing system comprises one or more processors and one or more computing devices comprising instructions that, when executed by the one or more processors are configured to perform operations. The operations comprise providing a computer network with the one or more computing devices that are interconnected through the computer network. The operations comprise providing a computer network with the one or more computing devices that are interconnected through the computer network. The operations comprise submitting a proposal related to a healthcare record from a first computing device of the one or more computing devices to a plurality of endorsing peers for approval, each of the endorsing peers comprising at least one computing device. The operations comprise approving the proposal by the plurality of endorsing peers with the at least one computing device and replying to the proposal with a response comprising a peer approved transaction. The operations comprise creating a private peer-to-peer communication channel between the first computing device and a second computing device and transmitting data related to the healthcare record from the first computing device to the second computing device through the private peer-to-peer communication channel. The operations comprise creating a block of transactions based on the data transmitted from the first computing device to the second computing device and adding the block of transactions to a ledger.

In some embodiments, creating the private peer-to-peer communication channel between the first computing device and the second computing device comprises storing the data in a private state database on peers of authorized organizations and the data is accessible in the private state database from a chaincode.

In some embodiments, creating the block of transactions comprises creating a hash value of the data and writing the hash value on a ledger of each of the peers of authorized organizations, wherein the ledger stores entries of the healthcare records that are invoked by the one or more computing devices.

In some embodiments, the ledger comprises a first smart contract that is assigned to a first peer on the first computing device and a second smart contract that is assigned to a second peer on the second computing device.

In some embodiments, the private peer-to-peer communication channel is created after one or more of the first smart contract or the second smart contract are approved by the plurality of endorsing peers.

In some embodiments, the first computing device comprises a display that is configured to display information related to the healthcare record.

In some embodiments, creating the private peer-to-peer communication channel comprises using a communication channel to exchange information to allow a connection over a secured API to be formed to exchange the data.

Additional features and advantages of the embodiments disclosed herein will be set forth in the detailed description that follows, and in part will be clear to those skilled in the art from that description or recognized by practicing the embodiments described herein, including the detailed description which follows, the claims, as well as the appended drawings. It is to be understood that both the foregoing general description and the following detailed description present embodiments intended to provide an overview or framework for understanding the nature and character of the embodiments disclosed herein. The accompanying drawings are included to provide further understanding and are incorporated into and constitute a part of this specification. The drawings illustrate various embodiments of the disclosure, and together with the description explain the principles and operations thereof.

BRIEF DESCRIPTION OF THE DRAWINGS

These and other features, embodiments and advantages are better understood when the following detailed description is read with reference to the accompanying drawings, in which.

DETAILED DESCRIPTION

Figure 1:
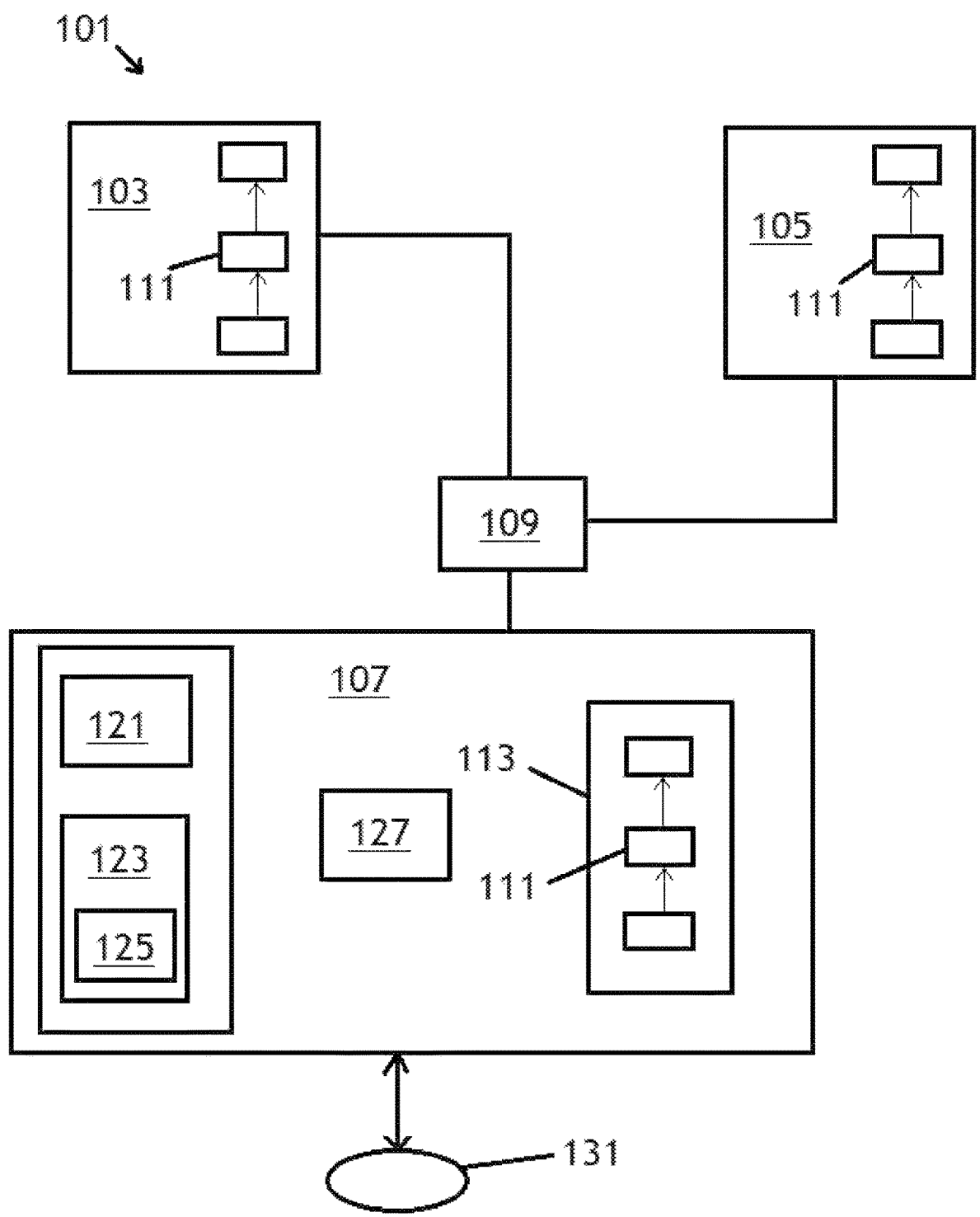
FIG. 1 schematically illustrates example embodiments of a computing system in accordance with embodiments of the disclosure.

Embodiments will now be described more fully hereinafter with reference to the accompanying drawings in which example embodiments are shown. Whenever possible, the same reference numerals are used throughout the drawings to refer to the same or like parts. However, this disclosure may be embodied in many different forms and should not be construed as limited to the embodiments set forth herein.

As used herein, the term "about" means that amounts, sizes, formulations, parameters, and other quantities and characteristics are not, and need not be, exact, but may be approximate and/or larger or smaller, as desired, reflecting tolerances, conversion factors, rounding off, measurement error and the like, and other factors known to those of skill in the art.

Ranges can be expressed herein as from "about" one value, and/or to "about" another value. When such a range is expressed, another embodiment includes from the one value to the other value. Similarly, when values are expressed as approximations by use of the antecedent "about," it will be understood that the value forms another embodiment. It will be further understood that the endpoints of each of the ranges are significant both in relation to the other endpoint, and independently of the other endpoint.

Directional terms as used herein—for example up, down, right, left, front, back, top, bottom, upper, lower, etc.—are made only with reference to the figures as drawn and are not intended to imply absolute orientation.

Unless otherwise expressly stated, it is in no way intended that any method set forth herein be construed as requiring that its steps be performed in a specific order, nor that with any apparatus, specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

As used herein, the singular forms "a," "an" and "the" include plural references unless the context clearly dictates otherwise. Thus, for example, reference to "a" component includes aspects having two or more such components, unless the context clearly indicates otherwise.

The word "exemplary," "example," or various forms thereof are used herein to mean serving as an example, instance, or illustration. Any aspect or design described herein as "exemplary" or as an "example" should not be construed as preferred or advantageous over other aspects or designs. Furthermore, examples are provided solely for purposes of clarity and understanding and are not meant to limit or restrict the disclosed subject matter or relevant portions of this disclosure in any manner. It can be appreciated that a myriad of additional or alternate examples of varying scope could have been presented but have been omitted for purposes of brevity.

As used herein, the terms "comprising" and "including", and variations thereof, shall be construed as synonymous and open-ended, unless otherwise indicated. A list of elements following the transitional phrases comprising or including is a non-exclusive list, such that elements in addition to those specifically recited in the list may also be present.

The terms "substantial," "substantially," and variations thereof as used herein are intended to represent that a described feature is equal or approximately equal to a value or description. For example, a "substantially planar" surface is intended to denote a surface that is planar or approximately planar. Moreover, "substantially" is intended to denote that two values are equal or approximately equal. In some embodiments, "substantially" may denote values within about 10% of each other, such as within about 5% of each other, or within about 2% of each other.

Modifications may be made to the instant disclosure without departing from the scope or spirit of the claimed subject matter. Unless specified otherwise, "first," "second," or the like are not intended to imply a temporal aspect, a spatial aspect, an ordering, etc. Rather, such terms are merely used as identifiers, names, etc. for features, elements, items, etc. For example, a first device and a second device generally correspond to device A and device B or two different or two identical devices or the same device.

The claimed subject matter is now described with reference to the drawings. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

The present disclosure relates to recording and/or analyzing medication request transactions in real-time. For example, referring to FIG. 1, in some embodiments, a computing system 101 is provided for recording and/or analyzing healthcare record transactions in real-time. The computing system 101 may comprise hardware and software components for recording, monitoring, analyzing, etc. the healthcare record transactions. For example, in some embodiments, the computing system 101 can comprise one or more computing devices, for example, a first computing device 103, a second computing device 105, a third computing device 107, etc. In some embodiments, the computing devices 103, 105, 107 can be part of a blockchain architecture and may be interconnected over a computer network 109. As used herein, the computer network (e.g., or computer network, computing network, etc.) can comprise a wide area network (e.g., "WAN"), a local area network (e.g., "LAN"), peer-to-peer networks, the internet, etc. The computer network 109 can be provided with one or more computing devices 103, 105, 107 that may be interconnected through the computer network 109. By being interconnected, the one or more computing devices 103, 105, 107 can transmit data, information, etc. between computing devices 103, 105, 107 through the computer network 109. In some embodiments, the computing devices 103, 105, 107 can comprise a computer terminal or computer workstation. The computing devices 103, 105, 107 can comprise, for example, a desktop computer, a laptop computer, a mobile computing device (e.g., a smartphone, a tablet, etc.). For example, the first computing device 103 can be connected to the network 109, the second computing device 105 can be connected to the network 109, and the third computing device 107 can be connected to the network 109. In some embodiments, the computing devices 103, 105, 107 can each store and maintain a blockchain 111 (e.g., described below). While three computing devices 103, 105, 107 are illustrated in FIG. 1, any number (e.g., one or more) of computing devices can be provided as part of the computing system 101 and connected to the network 109. By being connected to the network 109, the computing devices 103, 105, 107 can send and/or receive information (e.g., data, instructions, etc.) to and/or from the network 109 and the other computing devices.

In some embodiments, one or more of the computing devices 103, 105, 107, etc. can be substantially similar or identical to the third computing device 107. For example, the third computing device 107 can comprise the blockchain 111 that may be stored within a hardware storage device 113. The third computing device 107 can comprise a processor 121 and memory 123 (e.g., a computer-readable data storage medium that can store data). The processor 121 can execute a computer-executable code 125 (e.g., instructions, etc.) to perform methods described herein. In some embodiments, the third computing device 107 can comprise a display 127 that can display information to a user 131 (e.g., medical personnel, a patient, insurer, pharmacist, hospital, etc.). In some embodiments, the third computing device 107 can be configured to receive user input from the user 131 (e.g., which can direct operations of the blockchain 111) and can display information (e.g., related to the blockchain, health-care record transactions, etc.) to the user 131. Accordingly, as used herein, the computing system 101 can perform operations, tasks, and functions that may comprise computer-executed, computerized, software-implemented, or computer-implemented tasks. Similarly, the functions and methods described herein may be performed by several types of hardware, software, firmware, etc. components that may carry out the specified functions. In some embodiments, the computing system 101 and the computing devices 103, 105, 107 may comprise integrated circuit components (e.g., memory elements, digital signal processing elements, logic elements, look-up tables, etc.) that may perform a variety of functions under the control of a processor, microprocessor, or other control devices.

Figure 2:
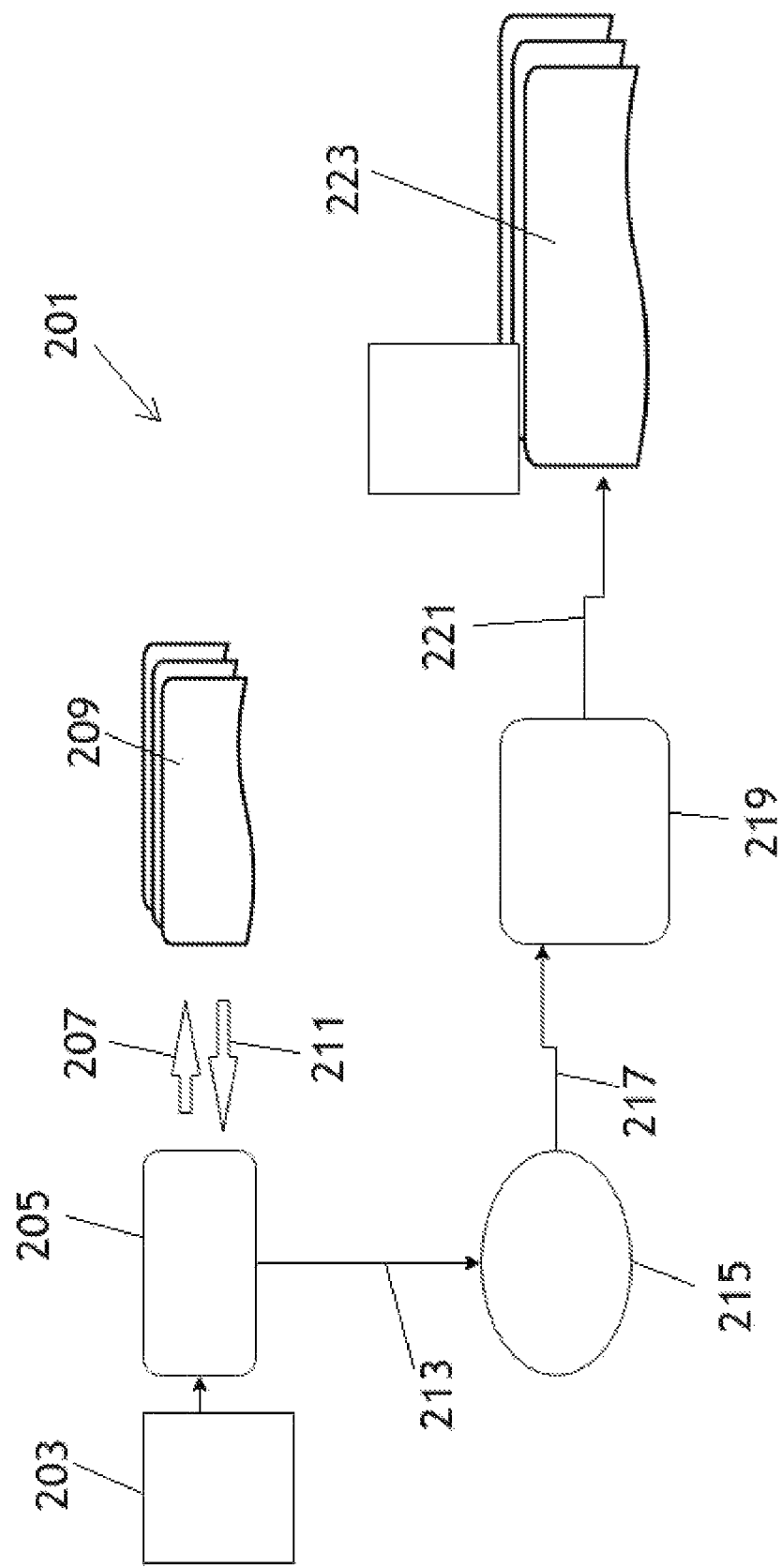
FIG. 2 illustrates example embodiments of a computer-implemented method in accordance with embodiments of the disclosure.

Referring to FIG. 2, embodiments of a computer-implemented method 201 are illustrated. In some embodiments, the computer-implemented method 201 can comprise a computing device 203 that may be substantially identical to the computing devices 103, 105, 107 illustrated and described in FIG. 1. The computer-implemented method 201 can comprise a healthcare record transaction, for example. In some embodiments, the computing device 203 can be used by a user (e.g., the user 131 comprising medical personnel, a patient, insurer, pharmacist, hospital, etc.). Initially, the computing device 203 can invoke a transaction via an application SDK/API 205. As used herein, an API may comprise a communication protocol and/or an interface that facilitates communication with different parts of a software component. As used herein, an SDK may comprise a collection of software development tools in one or more installable packages. Once a transaction has been invoked, the application SDK/API 205 can submit a proposal at 207 to one or more endorsing peers 209. In some embodiments, the endorsing peers can simulate the transaction and may endorse the transaction if smart contracts are fulfilled. A response 211 may be transmitted from the endorsing peers to the application SDK/API 205. If the response 211 comprises an endorsement of the submitted proposal 207, then the application SDK/API 205 can transmit a submission 213 comprising one or more peer approved transactions 215. In some embodiments, the peer approved transactions 215 can be transmitted to an ordering service 219 wherein a block of transactions is created 217. Following the creation of the block of transactions, the block of transactions may be submitted 221 to one or more peers 223, whereupon endorsements can be verified. In this way, in some embodiments, methods can comprise submitting the proposal, which may be related to a healthcare record from a first computing device of the one or more computing devices 103, 105, 107, to a plurality of endorsing peers for approval, wherein each of the endorsing peers can comprise at least one computing device 103, 105, 107. Likewise, in some embodiments, methods can comprise approving the proposal by the plurality of endorsing peers with the at least one computing device 103, 105, 107 and replying to the proposal with a response comprising a peer approved transaction. In some embodiments creating a private peer-to-peer communication channel can comprise using a communication channel to exchange information to allow a connection over a secured API to be formed to exchange the data.

As an example, a doctor may seek treatment for a patient who is suffering from a malady. Initially, the doctor may use the computing device 203 to invoke a transaction, for example, by contacting a group offering treatment. Information related to the transaction between the doctor and the group may be transmitted at 207 to the one or more endorsing peers 209. The information may comprise, for example, patient information (e.g., name, location, etc.), malady, etc. Next, the one or more endorsing peers 209 may endorse the proposal provided that the doctor is valid and authorized to provide such a proposal. The endorsement of the proposal may be transmitted as a response 211, whereupon the doctor and the group form an agreement at 213, 215. In some embodiments, the block (e.g., that is one step in a ledger) may be created at 219, followed by a final check at 223.

Figure 3:
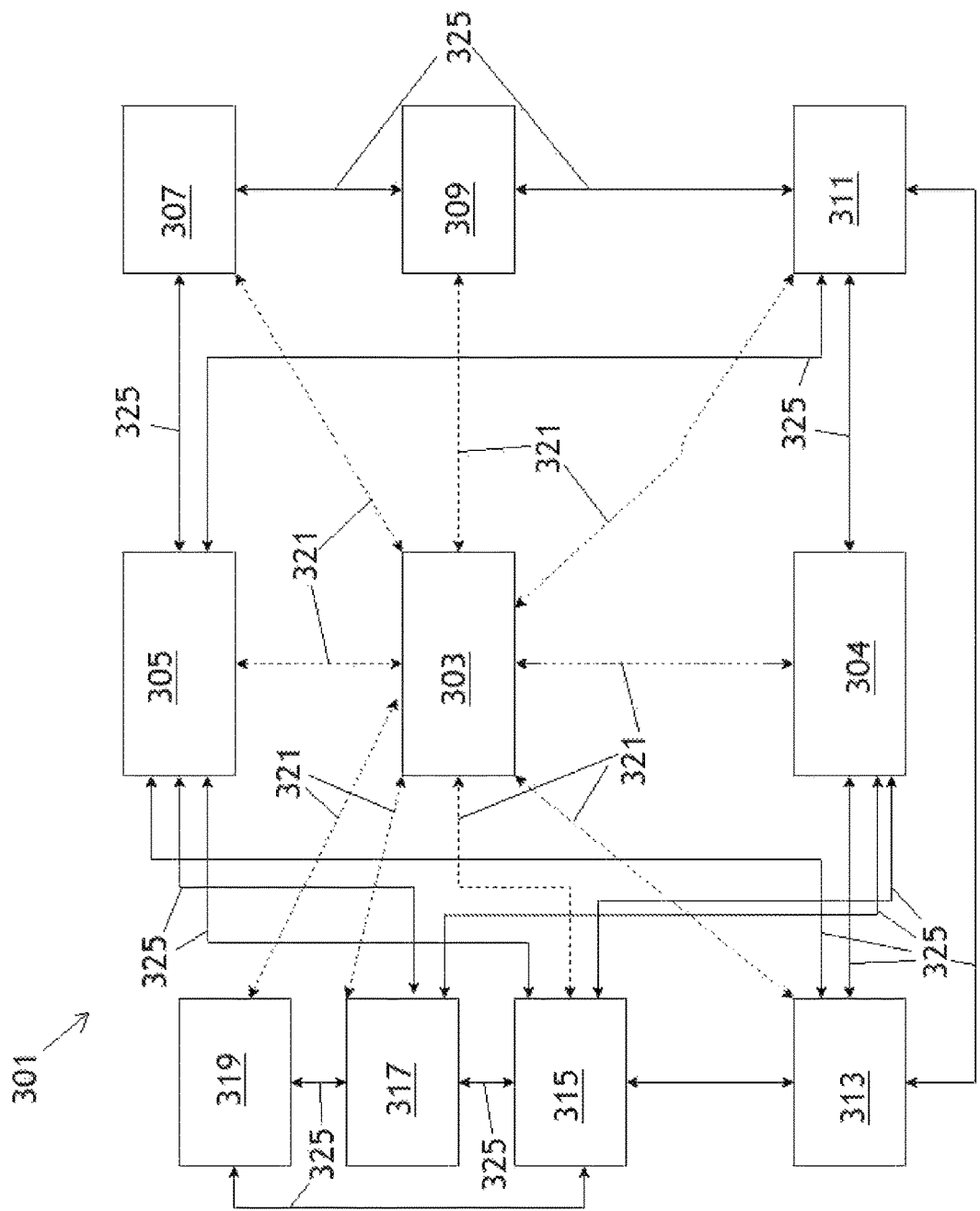
FIG. 3 illustrates example embodiments of a computing network in accordance with embodiments of the disclosure.

Referring to FIG. 3, embodiments of a computing network 301 for managing health care records. The computing network 301 may comprise, for example, a decentralized network in which the management of the health care records may be coordinated between various parties within the computing network 301. For example, the computing network 301 may comprise a scriptlock (e.g., hereinafter "computing system") peer node 303. The peer node 303 can communicate with one or more other peer nodes, for example, one or more of the following peer nodes: a patient 304, a drug manufacturer 305, government agencies such as the U.S. Department of Health 307 or the Office of Pharmacy Affairs 309, a covered entity 311, a contract pharmacy 313, a third party payor 315, a state Medicaid department 317, and/or the Centers for Medicare and Medicaid Services (e.g., "CMS") 319. In some embodiments, the computing network 301 can comprise an endorsement transaction pipeline 321 that facilitates communication between the peer node 303 and the other peer nodes 305, 307, 309, 311, 313, 315, 317, and/or 319. In some embodiments, the computing network 301 can comprise a private channel communication 325 that facilitates communication between the other peer nodes 305, 307, 309, 311, 313, 315, 317, and/or 319. For example, as used herein, in some embodiments, the private channel communication 325 can be used such that methods can comprise creating a private peer-to-peer communication channel (e.g., 325, 217/219, etc.) between the first computing device and the second computing device and transmitting data (e.g., 215, 217, etc.) related to the healthcare record from the first computing device to the second computing device through the private peer-to-peer communication channel.

The present application may be implemented within a computer network, for example, a clustered network environment comprising one or more computing devices that may be coupled over a network that facilitates communication between the various computing devices. The computing devices may comprise, for example, one or more of a client device, a personal computer (PC), a mobile device, computing devices used for storage, and other types of computers that may be coupled via a network connection. The network connection may comprise, for example, one or more of a local area network (LAN) or a wide area network (WAN), for example, that utilizes Network Attached Storage (NAS) protocols, such as a Common Internet File System (CIFS) protocol or a Network File System (NFS) protocol to exchange data packets, a Storage Area Network (SAN) protocol, such as Small Computer System Interface (SCSI) or Fiber Channel Protocol (FCP), an object protocol, such as S3, etc.

In some embodiments, the software may provide an API and one or more SDKs to allow organizations involved in an industry, for example, the healthcare industry, to record and track medical requests in a workflow. In some embodiments, the software may use IBM's Hyperledger Fabric distributed ledger product to persist records in a cryptographically secure means in a ledger. As used herein, the term cryptographically secure may comprise a technique for secure communication (e.g., communication between a first party and a second party that is withheld from a third party) in the presence of one or more third parties. In some embodiments, the service may use software enforced business logic known as smart contracts to drive a compliance component. As used herein, a smart contract may comprise a computer protocol that is intended to digitally facilitate, verify, or enforce the negotiation or performance of a contract (e.g., by allowing the performance of a transaction without a third party). This component may alert the organization or deny the recording of a record if the rules of a contract are violated. In addition, contracts may trigger events and messaging based on the data in a transaction interacting with the rules of the contract. For example, in some embodiments, the service may comprise an optional component that requires organizations to format their data according to the HL7 FHIR release 4 standard for recording medical requests in a healthcare workflow. In some embodiments, the service can provide inherent HL7 FHIR compliance for organizations through an HL7 FHIR form builder that is built within the service. For example, the service may create FHIR form builders for organizations that allow compliance with the HL7 FHIR release 4 standard without additional work for the organizations (e.g., additional APIs, building, etc.). As such, in these embodiments, the organizations may be brought into compliance with the HL7 FHIR release 4 standard without additional work required for the organization.

In some embodiments, the present application can be installed by a vendor onto a healthcare organization's devices. In addition, or in the alternative, in other embodiments, the present application can be offered as a cloud-based service that may be hosted in a secure cloud service such as Amazon Web Services. The healthcare organization may integrate the service by allowing their own software to integrate the SDKs or by allowing their own software to securely connect to the service's API. If an SDK is used, the SDK can expose methods that allow the host software to connect to the subject computing system application. Alternatively, secure API endpoints may be used to access the subject computing system application.

When a new organization enrolls with the subject computing system service, the subject computing system can create a primary node for the organization. A primary node can comprise a ledger, a transaction orderer, a certificate authority, subject computing system Smart Contracts, and a client application.

Creating a primary node can proceed as follows. Initially, the first step in creating a primary node can comprise the Certificate Authority (e.g., "CA") generating a Membership Service Provider (MSP). A certificate authority creates and manages all identities that may access the node. An identity is a set of certificates that grant permissions to request that the application create, store, verify, or append data that will be entered into the ledger.

An MSP abstracts away all cryptographic mechanisms and protocols behind issuing certificates, validating certificates and user authentication. An MSP may define their own notion of identity, and the rules by which those identities are governed (identity validation) and authenticated (signature generation and verification).

Once the certificate authority has generated an MSP, the CA orderer adds the node to the MSP. Once the orderer node has been added to the MSP, the orderer node will have permission to generate a ledger and add the first block on the organization's ledger. A block is an immutable collection of transactions. Once a block has been added to the ledger, it cannot be removed without breaking the ability to cryptographically verify the contents of the ledger. The first block is called the genesis block. The genesis block of the subject computing system ledger contains the initial configuration details of the node describing the permissions dictated by the MSP, the base configuration for the client application and the configuration details for the orderer node itself.

The ledger can comprise the sequenced, tamper-resistant record of all state transitions in the fabric. State transitions are a result of chaincode invocations ('transactions') submitted by participating parties. Each transaction results in a set of asset key-value pairs that are committed to the ledger as creates, updates, or deletes. The ledger is comprised of a blockchain ('chain') to store the immutable, sequenced record in blocks, as well as a state database to maintain current fabric state. There is one ledger per channel. Each peer maintains a copy of the ledger for each channel of which they are a member.

The following are features and/or definitions of a HyperLedger.

Query and update ledger using key-based lookups, range queries, and composite key queries.

Read-only queries using a rich query language (if using Couch DB as state database).

Read-only history queries—Query ledger history for a key, enabling data provenance scenarios.

Transactions consist of the versions of keys/values that were read in chaincode (read set) and keys/values that were written in chaincode (write set).

Transactions contain signatures of every endorsing peer and are submitted to ordering service.

Transactions are ordered into blocks and are "delivered" from an ordering service to peers on a channel.

Peers validate transactions against endorsement policies and enforce the policies.

Prior to appending a block, a versioning check is performed to ensure that states for assets that were read have not changed since chaincode execution time.

There is immutability once a transaction is validated and committed.

A channel's ledger contains a configuration block defining policies, access control lists, and other pertinent information.

Channels contain Membership Service Provider instances allowing for crypto materials to be derived from different certificate authorities.

The following are features and/or definitions related to an identity.

The different actors in a blockchain network include peers, orderers, client applications, administrators and more. Each of these actors—active elements inside or outside a network able to consume services—has a digital identity encapsulated in an X.509 digital certificate. These identities really matter because they determine the exact permissions over resources and access to information that actors have in a blockchain network.

A digital identity furthermore has some additional attributes that Fabric uses to determine permissions, and it gives the union of an identity and the associated attributes a special name—principal.

Principals are just like userIDs or groupIDs, but a little more flexible because they can include a wide range of properties of an actor's identity, such as the actor's organization, organizational unit, role or even the actor's specific identity. When we talk about principals, they are the properties which determine their permissions.

For an identity to be verifiable, it must come from a trusted authority. A membership service provider (MSP) is that trusted authority in Fabric. More specifically, an MSP is a component that defines the rules that govern the valid identities for this organization. The default MSP implementation in Fabric uses X.509 certificates as identities, adopting a traditional Public Key Infrastructure (PKI) hierarchical model (more on PKI later).

The following are features and/or definitions related to a Certificate Authority.

A Certificate Authority dispenses certificates to different actors. These certificates are digitally signed by the CA and bind together the actor with the actor's public key (and optionally with a comprehensive list of properties). As a result, if one trusts the CA (and knows its public key), it can trust that the specific actor is bound to the public key included in the certificate, and owns the included attributes, by validating the CA's signature on the actor's certificate.

Certificates can be widely disseminated, as they do not include either the actors' nor the CA's private keys. As such they can be used as anchors of trusts for authenticating messages coming from different actors.

CAs also have a certificate, which they make widely available. This allows the consumers of identities issued by a given CA to verify them by checking that the certificate could only have been generated by the holder of the corresponding private key (the CA).

In a blockchain setting, every actor who wishes to interact with the network needs an identity. In this setting, you might say that one or more CAs can be used to define the members of an organization from a digital perspective. It's the CA that provides the basis for an organization's actors to have a verifiable digital identity.

The following are features and/or definitions related to Membership and Policies.

This is where a Membership Service Provider (MSP) comes into play—it identifies which Root CAs and Intermediate CAs are trusted to define the members of a trust domain, e.g., an organization, either by listing the identities of their members, or by identifying which CAs are authorized to issue valid identities for their members, or—as will usually be the case—through a combination of both.

The power of an MSP goes beyond simply listing who is a network participant or member of a channel. An MSP can identify specific roles an actor might play either within the scope of the organization the MSP represents (e.g., admins, or as members of a sub-organization group), and sets the basis for defining access privileges in the context of a network and channel (e.g., channel admins, readers, writers).

The configuration of an MSP is advertised to all the channels where members of the corresponding organization participate (in the form of a channel MSP). In addition to the channel MSP, peers, orderers, and clients also maintain a local MSP to authenticate member messages outside the context of a channel and to define the permissions over a particular component (who has the ability to install chaincode on a peer, for example).

Policies allow members to decide which organizations can access or update a Fabric network and provide the mechanism to enforce those decisions. Policies contain the lists of organizations that have access to a given resource, such as a user or system chaincode. They also specify how many organizations need to agree on a proposal to update a resource, such as a channel or smart contracts. Once they are written, policies evaluate the collection of signatures attached to transactions and proposals and validate if the signatures fulfill the governance agreed to by the network.

The following are features and/or definitions related to a system channel configuration.

Every network begins with an ordering system channel. There must be exactly one ordering system channel for an ordering service, and it is the first channel to be created. The system channel also contains the organizations who are the members of the ordering service (ordering organizations) and those that are on the networks to transact (consortium organizations). The policies in the ordering system channel configuration blocks govern the consensus used by the ordering service and define how new blocks are created. The system channel also governs which members of the consortium are allowed to create new channels.

The following are features and/or definitions related to Application Channel Configuration.

Application channels are used to provide a private communication mechanism between organizations in the consortium.

The policies in an application channel govern the ability to add or remove members from the channel. Application channels also govern which organizations are required to approve a chaincode before the chaincode is defined and committed to a channel using the Fabric chaincode lifecycle. When an application channel is initially created, it inherits all the ordering service parameters from the orderer system channel by default. However, those parameters (and the policies governing them) can be customized in each channel.

The following are features and/or definitions related to Access Control Lists (ACLs).

Network administrators will be especially interested in the Fabric's use of ACLs, which provide the ability to configure access to resources by associating those resources with existing policies. These "resources" could be functions on system chaincode (e.g., "GetBlockByNumber" on the "qscc" system chaincode) or other resources (e.g., who can receive Block events). ACLs refer to policies defined in an application channel configuration and extends them to control additional resources.

The following are features and/or definitions related to Smart Contract Endorsement Policies.

Every smart contract inside a chaincode package has an endorsement policy that specifies how many peers belonging to different channel members need to execute and validate a transaction against a given smart contract in order for the transaction to be considered valid. Hence, the endorsement policies define the organizations (through their peers) who must "endorse" (i.e., approve of) the execution of a proposal.

The following are features and/or definitions related to Modification policies.

There is one last type of policy that is crucial to how policies work in Fabric, the Modification policy. Modification policies specify the group of identities required to sign (approve) any configuration update. It is the policy that defines how the policy is updated. Thus, each channel configuration element includes a reference to a policy which governs its modification.

The following are features and/or definitions related to Peer Nodes.

Peer nodes are a fundamental element of the network because they host ledgers and smart contracts. They expose a set of APIs that enable administrators and applications to interact with the services that they provide.

The following are features and/or definition related to organization nodes.

Each client that joins the subject computing system network will receive an organization node. Each organization node will have its own MSP to describe the users in that organization and their roles and privileges. Every organization node will also have its own set of Smart Contracts that will dictate what modification abilities an organization will have. These contracts will also dictate what requirements an organization has in order to verify and endorse a transaction entered into the ledger.

The following are features and/or definitions related to Oracle Nodes.

Oracle nodes are hosted by the subject computing system and allow the subject computing system to monitor transactions submitted by organization nodes.

The following are features and/or definitions related to Channels.

Channels allow a specific set of peers and applications to communicate with each other within a network. A channel must consist of a minimum of two organization nodes, their associated applications, and an orderer node. The organizations in a channel may create transactions and perform any modification or endorses smart contracts. The orderer node in a channel will monitor and record transactions on a temporary ledger that exists only in the channel. In the event that the organization nodes in a channel wish to add their data to the main network ledger, the orderer will coordinate sending all transactions created in the channel to the rest of the network for verification and endorsement.

The following are features and/or definitions related to Private Data Collections.

In cases where a group of organizations on a channel need to keep data private from other organizations on that channel, they have the option to create a new channel comprising of just the organizations who need access to the data. A private data collection is the combination of two element. First, the actual private data, sent peer-to-peer via gossip protocol to only the organization(s) authorized to see it. This data is stored in a private state database on the peers of authorized organizations, which can be accessed from chaincode on these authorized peers. The ordering service is not involved here and does not see the private data. Note that because gossip distributes the private data peer-to-peer across authorized organizations, it is required to set up anchor peers on the channel, and configure CORE_PEER_GOSSIP_EXTERNALENDPOINT on each peer, in order to bootstrap cross-organization communication. Second, a hash of that data, which is endorsed, ordered, and written to the ledgers of every peer on the channel. The hash serves as evidence of the transaction and is used for state validation and can be used for audit purposes.

The following are features and/or definitions related to Peer Identity.

All peers have an identity assigned to them via a digital certificate from a particular certificate authority. When interacting in the network, each peer's MSP will share information regarding the identity and abilities of the peer. Whenever a peer connects using a channel to a blockchain network, a policy in the channel configuration uses the peer's identity to determine its rights. The mapping of identity to organizations is provided by the channel's MSP.

The following are features and/or definitions related to peers, consensus, transactions, and orderer nodes.

Peer Consensus, the mechanism by which applications and peers interact with each other to ensure that every peer's ledger is kept consistent with each other is mediated by special nodes called orderers.

Peers may use their associated application to create update or query transactions. Updating transactions create data to be entered into the ledger. Query transactions query the existing ledger to obtain a subset of data. An update transaction is quite different from a query transaction because a single peer cannot, on its own, update the ledger—updating requires the consent of other peers in the network. A peer requires other peers in the network to approve a ledger update before it can be applied to a peer's local ledger. This process is called consensus, which takes much longer to complete than a simple query. But when all the peers required to approve the transaction do so, and the transaction is committed to the ledger, peers will notify their connected applications that the ledger has been updated.

A series of steps are provided for peers to propose an update transaction, endorse the transaction, validated the transaction and finally to write the transaction into the immutable distributed ledger.

In the first phase, applications work with a subset of endorsing peers, each of which provide an endorsement of the proposed ledger update to the application, but do not apply the proposed update to their copy of the ledger. In the second phase, these separate endorsements are collected together as transactions and packaged into blocks. In the third and final phase, these blocks are distributed back to every peer where each transaction is validated before being committed to that peer's copy of the ledger.

The following are features and/or definitions related to the subject computing system Network Services.

The subject computing system may be HL7 FHIR formatted, HIPAA compliant cryptographically secure distributed ledger storage. A copy of each ledger is located on each peer in the network. Ledger data may be queried, based on permission level of peers to create reporting. Data is scrubbed to de-identify PII and PHA.

For example, in some embodiments, the subject computing system can provide for information related to social risk factors (e.g., housing, instability, food insecurity, etc.) to be easily exchanged in real-time and integrated within the ledge to allow for better health outcomes to be achieved, which is an improvement over past attempts. In some embodiments, the blockchain platform can provide an inherent Document Requirement Lookup Service (e.g., "DRLS") that can be integrated into a provider's EHR, which can allow providers to confirm patient data (e.g., social risk factors such as housing, instability, food security as well as prior authorizations, etc.) in real-time. This can, in some embodiments, eliminate the normal delays involved with obtaining prior authorizations within the current legacy systems. In some embodiments, the computer-implemented system can allow prior authorizations to be exchanged in real-time within the existing workflow. For example, by exchanging within the existing workflow, changes or additions within the current legacy systems may not need to be made. Further, the integrity of the data being exchanged through the blockchain encryption may further be maintained. In some embodiments, smart contracts and the blockchain platform can eliminate the need to use certain technology (e.g., facsimile or "fax") across healthcare platforms.

The following are features and/or definitions related to the subject computing system Proprietary compliance endorsement and modification policy smart contracts. Data Modification Smart Contracts: (1) Healthcare provider adding a customer; (2) Dr. prescribing a drug to a customer; (3) Pharmacy acknowledging a prescription. (4) Pharmacy distributing a prescription to a customer.

The following are features and/or definitions related to compliance verification and endorsement smart contract.

340B Flags: 340B issues facing drug manufacturers, PBM's, governmental agencies, and hospital systems (e.g. through defined ledger transaction conflicts between all such entities as no such technology currently offers a real-time/point of sale solution).

OARS Flags: Prescriber compliance with state and federal opioid/narcotic/scheduled drug input and monitoring pursuant to state and federal guidelines for the same such as the 30/60/90 day rules for such prescriptions (e.g. through defined ledger transaction conflicts between prescribers and the applicable state and federal tracking systems).

HIPAA Flags: HIPAA violations/breaches (e.g. through defined ledger transaction conflicts between Covered Entities, Business Associates, Subcontractors (as such terms are defined by HIPAA), and any other entity or entities required to adhere to HIPAA standards).

CMS/Fraud Waste & Abuse (FWA) Issues: CMS Fraud, Waste, and Abuse issues (e.g. through defined ledger transaction conflicts between hospital systems, provers/prescribers, PBM's and pharmacies/PSAO's, pharmacies and CMS or any other state/federal prescription tracking system).

Opioid Flags: Opioid/narcotic/scheduled drug tracking/monitoring (e.g. through defined ledger transaction conflicts between all entities/persons required to submit, track, and monitor such data within the state and federal tracking systems such as Ohio's OARS system).

Audit Flags: Duplicative prescriptions (e.g. through defined ledger transaction conflicts between the provider/prescriber and pharmacy, or pharmacy and PBM clinical staff); (3) CMS Fraud, Waste, and Abuse issues (e.g. through defined ledger transaction conflicts between hospital systems, provers/prescribers, PBM's and pharmacies/PSAO's, pharmacies and CMS or any other state/federal prescription tracking system).

Drug pricing transparency (e.g. through defined ledger transaction conflicts between PBM's and clients/health plans, drug manufacturers and PBM's, and pharmacies and PSAO's).

The following are features and/or definitions related to the subject computing system's proprietary oracle nodes used for monitoring and alerting.

Drug interactions Oracle: This node will monitor incoming modification transactions involving the prescription of a drug emitted from organization nodes. It will review past transactions within a specific time frame to locate pre-existing prescription transactions involving a specific patient. The oracle will use a list of dangerous drug interactions between the current prescription and past. If there is a bad interaction discovered, the oracle can be configured to alert peers in the network and/or decline to endorse a transaction.

The following are features and/or definitions related to an Audit Oracle.

The audit oracle allows organizations to save time and improve efficiencies as the subject computing system application will allow for customizable oracle builds for audit records which can allow for better data dictionary views to track suspicious activities.

The following are features and/or definitions related to Oracle Builder.

The oracle builder allows organizations to save time and improve efficiencies as the subject computing system application will allow for customizable oracle builds based upon the oracle functionality throughout the subject computing system application.

The following are features and/or definitions related to Marketing Reporting Dashboard Builder.

The marketing reporting dashboard builder allows organizations to save time and improve marketing performance by enabling the organization to customize unique reporting analytics fit for its individual needs based upon the data pulled from the application dashboard.

The following are features and/or definitions related to the subject computing system client application and secure API. In some embodiments, each organization peer on the network will get its own subject computing system application interface allowing them to interact with the subject computing system network by adding. Querying, endorsing, and verifying data is submitted to the network. In addition to interacting with the network, a subject computing system application will allow organizations to ensure their data conforms to the HL7 FHIR v4 specification if they choose to. In some embodiments, as stated herein, benefits may be achieved with the subject computing system due to the inherent HL7 FHIR v4 specification compliance with the subject computing system. In some embodiments, subject computing system can provide HL7 FHIR Bulk (e.g., "Flat FHIR") specification capabilities. This specification can allow one or more organizations (e.g., payers, providers, etc.) to efficiently exchange information for one or more individuals (e.g., patients) at one time allowing the individuals to take their information with them as they move from one organization (e.g., payer or provider) to another. In some embodiments, the Initial SDK is written in javascript.

In some embodiments, HTTPS Secure Restful Endpoints require header authentication signatures.

In some embodiments, one or more of the following commands are available for each subject computing system Application: Submit Transaction; Query Ledger; Create Channel; View Event History; and/or Monitor Events. Each application may be aware of the policies set up on each organization and the subject computing system node.

The initial network setup may proceed as follows. First, the subject computing system will establish an orderer node. Next, the subject computing system will establish a Certificate Authority. Next, the subject computing system will establish a network Membership Service Provider. Next, the subject computing system will set up an organization peer for each customer and configure their specific. smart contracts per a traditional contract arranged with the customer. Next, the subject computing system will provide an application interface and user accounts for each organization. Next, the subject computing system will enable any subject computing system oracle nodes that apply for the specific network.

The subject computing system may provide improvements on pre-existing services. For example, current services centralize control of data. This makes interoperability difficult or impossible based on the relationship between healthcare organizations. This service employs a cryptographically secured distributed ledger system that allows all members of a network to verify data without having to be exposed to the details of the data. This allows for members of a network to share one stream of transactional data without compromising their privacy.

The subject computing system comprises several unique qualities. First, by positioning as an add-on system that is focused on risk and regulatory compliance and data interoperability using a distributed ledger network, the subject computing system offers the healthcare arena a unique and, more importantly, secure way to monitor and transfer data across multiple channels and organizations. For instance, by utilizing this unique application the subject computing system can offer services to any company within the healthcare arena that can: (1) increase interoperability by assisting organizations in ensuring data formats meet industry standards; (2) allow data to be shared or restricted across many organizations and channels using cryptographic techniques as well as industry standard security techniques; (3) allow organizations to setup alerts when data transactions in one ledger conflict with another organization's ledger; and (4) allow organizations to setup multiple contracts between several different organizations and such contracts can define what a ledger transaction conflict would look like (e.g. The state of Ohio's OARS tracking system would have different conflict concerns than a PBM would for the same transaction).

The subject computing system is not limited to the aforementioned uses and/or applications. Rather, in some embodiments, other possible uses for the subject computing system are envisioned. For example, the techniques used in this service could be used in any industry in which members of a network may wish to verify the transactional data in the network without sharing the specifics of the data.

Flow Diagram Key and Explanation

DM—Drug Manufacturer/Wholesaler
HHS—US Dept. of Health & Human Services
OPA—Office of Pharmacy Affairs
CE—Covered Entity
P—Patient
CP—Contract Pharmacy
$3^{rd}$ PP—$3^{rd}$ Party Payor (PBM, Insurance, etc.)
SMS—State Medicaid System/Program
SL—ScriptLock (e.g., the subject computing system)

An explanation of relationships may carry out as follows. Initially, it is noted that the CE may comprise healthcare providers, community-based organizations, behavioral health networks, etc. For example, the CE may comprise these three groups as part of the healthcare delivery journey.

P's receive healthcare services from different CE's at different dates, times, and locations.

P's health information is then sent from the respective CE's to the subject computing system peer node through the subject computing system Endorsement Transaction Pipeline.

Once P's health information is sent from the respective CE's to the subject computing system peer node through the subject computing system Endorsement Transaction Pipeline, P's are then able to control the sharing of their health information by utilizing the subject computing system's private channel communication pipeline.

This exchange of health information will allow for the organic adoption of a nationwide health information infrastructure which will reduce the interoperability burdens within current legacy health systems, reduce overall health care costs, and ultimately improve patient care outcomes.

CE's register to participate in the 340B program (can register online the first 2 weeks of any calendar quarter) with OPA and when approved their listed on the OPA Information System (OPAIS) and eligible for participation the $1^{st}$ day of the next calendar quarter following the one which they completed the registration.

CE then contract with DM's (or wholesalers) to set up its 340B account

Duplicate Discount prohibition—prohibits DM's from giving a 340B discount and Medicaid FFS (Fee-for-service) rebate on the same drug.

CE's have different rules for "carving-in" FFS patients contingent on whether a CP isused:

For Drugs Dispensed by CP

CE may not "carve-in" FFS patients UNLESS the CE, SMP, and CP have established an arrangement to prevent "duplicate discounts" and notified the OPA of the arrangement.

For Drugs NOT Dispensed by CP

CE may "carve-in" drugs dispensed to registered outpatient locations or entity owned pharmacies (i.e. not a contract pharmacy) but the CE must inform the OPA of its decision and ensure the numbers it uses to bill 340B drugs to the SMS (i.e. National Provider Number (NPI) and/or state specific billing numbers).

These identifiers are listed on OPA's Medicaid Exclusion File which allows SMS agencies to exclude claims billed under these numbers from their rebate requests.

CE's Using CP's

CE is required to purchase the drugs and the CP provides some or all of the pharmacy services.

CE's using CP's should use a "ship to-bill to" procedure in which the CE purchases the drugs and the DM's bill the CE but ship the drugs directly to the CP.

CP's must provide the CE with quarterly financial statements, detailed status reports of collections, and a summary of receiving and dispensing records.

CE and CP's MUST establish and maintain a tracking system to prevent diversion of drugs to individuals who are not covered patients of the CE.

CE's are responsible for monitoring and compliance and ensuring CP's comply with the 340B requirements such as "patient definition" and "duplicate discount prohibition."

Many CE's use software to help with this tracking and compliance requirement.

DM's

The Federal Medicaid Rebate Program requires DM's to enter into a rebate agreement with HHS as a precondition for coverage of their drugs by Medicaid and Medicare Part B.

DM's must pay rebates to SMS's for "covered outpatient drugs" (i.e. 340B drugs).

The 340B rebate amount for a brand name covered drug is based in part on the DM's "best price" for the drug.

DM's enter into Pharmaceutical Pricing Agreements (PPA's) with CE's which require DM's to provide front-end discounts on covered drugs purchased by CE's.

DM's enter into rebate agreements with $3^{rd}$ PP's (i.e. PBM's) to provide discounts on drugs that are not 340B drugs and such rebate agreements PROHIBIT rebates on 340B drugs based upon the "duplicate discount prohibition" (see above).

$3^{rd}$ PP (PBM's, Insurance, Etc.)

PBM's contract with health plans or SMS's which have P's (patients/members).

PBM's also contract with CP's through Participating Pharmacy Agreements for better pricing based on pharmacy networks owned by the PBM.

PBM's offer a rebate to P's at the point of sale (POS) in the CP and then submit the rebate to the DM for reimbursement (some recoup the difference between the POS price minus any dispensing fees, etc. and the rebate recouped which is called "spread pricing").

In some embodiments, issues related to audits may arise. For example, PBM's don't provide claims level information to DM's and even if they did most PBM's do not have 340B identifiers in their system to differentiate what was/was not 340B drug utilization at the pharmacy level. Therefore, DM's may initially pass on a rebate for 340B drugs that would then need to be recouped through audit as such amounts are required to be paidback to SMS/CMS as its federal money.

However, DM's only have the information provided through the OPAIS (see above) as CP's ARENOT required to use to bill under the OPPS (Outpatient Prospective Payment System) and, therefore, are NOT required to use the CMS identifiers for 340B drugs that CE's would be required to use should it not use a CP for dispensing its 340B drugs (identifiers are JG & TB within the provider billing).

Accordingly, without a consistent set of claims fields and a standardized layout for States to use MILLIONS of dollars are wasted each year through duplicate discounts and overpayments of 340B drugs. Alternatively, PBM's are audited annually by DM's and could lose MILLIONS of dollars through the extrapolation of claims based upon a small volume of 340B inventory produced through an audit despite the fact that CP's may dispense non-340B drugs for which PBM's would rightfully earn rebates on and for which PBM's have already passed to the P's at the POS.

In some embodiments, a solution to problem 1 is as follows. The subject computing system platform alleviates the need for additional identifiers as it can create the unique hash in real-time in an unobtrusive manner in each step of the process and contracting relationship within the flow diagram.

Another situation that may arise relates to inoperability. For example, CE's and other health organizations struggle with operational efficiency due to interoperability challenges created by antiquated software and records communication barriers.

In some embodiments, a solution to this problem is as follows. The subject computing system platform provides a seamless integration into any existing records system and provides organizations the ability to connect their vast network of partners allowing them to exchange information in real time while ensuring immutability at each stage. The subject computing system platform is augmented by an IBM blockchain solution to enable CE's and other health organizations to enforce smart contracts without the need for the subject computing system to directly store or exchange any protected health information (PHI).

Additional benefits and improvements related to the subject computing system are as follows. For example, the subject computing system can use blockchain for recording metadata messages rather than fully storing phi. Metadata can comprise, for example, data the provides information about other data (e.g., descriptive metadata, structural metadata, administrative metadata, reference metadata, statistical metadata, etc.) such that metadata can be used to summarize basic information about data which can make tracking and working with specific data easier. In some embodiments, as part of the subject application, actual exchanges of data can occur in the private channels of the subject computing system. This can explain, in part, why hyper ledger may be used versus Ethereum. For example, by doing this, privacy and silo data may be preserved while allowing a map of how to find the data to be stored in the public chain. In the past, companies required a new model for all participants to buy into. In the present application, the subject computing system can allow existing systems to use the blockchain to build a topology of interconnected data while allowing the data to live in its old home while implementing FHIR. The data transferred over the public chain can be in the FHIR messaging formation, which may already be designed to use pointers to records. If a member of an organization desires to acquire the actual data behind the pointer, they can engage in a private peer-to-peer channel and exchange the data. The public chain can also be used to communicate updates to phi. If another member receives an event communicating an update, then they may receive a private channel with the member that made the update and receive the changes.

In some embodiments, the present application provides for the subject computing system peer channels to allow organizations to create a communication pipeline between members in the channel. The peer channel activity may be recorded in a shared ledger that can be viewed by all members of the channel as well as being verified by all members of the network. In some embodiments, while verifiers may only be able to see the hashes generated by the ledger, channel members may be able to view the data exchanged. As such, the subject computing system peer channels may only send anonymized request and response messages. These messages may adhere to the HL7 specification for request and response message types.

In some embodiments, if the members of a channel wish to exchange patient PHI or other HIPAA protected data, the subject computing system can allow members to create spontaneous private collection channels. The creation of these channels can be based on all members passing the smart contract business logic checks that may be specified by each member in the collection. Once members have agreed to join a private collection channel and have passed all of the required rules of engagement as set forth by each member's smart contract business logic checks, the subject computing system service can provide each member with a unique, short-lived API access token(s) as well as API endpoints for each member. The tokens can be used to allow secure data exchange between members via their API endpoints. In some embodiments, at this time, members may exchange data over the API secured with their tokens following the OAuth 2 specification. A minimal, anonymized audit log can be created during this process and may be added to the channel ledger to capture a high-level mapping of the activity that occurred in the exchanged. As such, no HIPAA protected data may be recorded in the audit log.

In some embodiments, the subject computing system can provide several FHIR HL7 tools that may assist member organizations in converting their data into the HL7 standard. For example, these tools may exist as a single page application front ends that may be combined with a backend application that can allow members to privately hook the tools into their data. The tools may consist of one or more of the following. First, the tools may comprise an HL7 field mapper. This tool can allow members to associate their existing data field types with the equivalent HL7 field type through a point and click interface. In some embodiments, members can choose which HL7 field type matches their existing field types. If HL7 does not have an equivalent field type, members may create custom field types. Custom field types can follow HL7 FHIR custom field specifications to ensure other members are able to view data captured for these fields. In some embodiments, all custom field types can be reviewed by admins of the subject computing system to ensure the field is truly custom.

In some embodiments, the tools may also consist of an HL7 profile form template builder. For example, once members have mapped their data to HL7 types, members may pull in their HL7 mapped fields into a form template structure in an ad hoc manner. In some embodiments, the tools may also comprise a profile form renderer. For example, once a member has created templates, the subject computing system can provide an endpoint that points to an actionable form built following the rules specified by the profile form template. Data submitted via these forms can be submitted over a TLS secured endpoint delivered directly to the member. No one including members of the subject computing system may have access to this data unless agreed upon by the member. In some embodiments, the tools may comprise HL7 profile template registries. For example, if a member chooses to do so, their templates can be shared via a template registry. The registry can contain blueprint files that can be used in a member's profile form renderer. Registries may exist at the full network level allowing all members in the network to access and use templates in the registry. Registries may exist at a channel level allowing only members of the channel to access and use templates in the registry.

It should be understood that while various embodiments have been described in detail relative to certain illustrative and specific examples thereof, the present disclosure should not be considered limited to such, as numerous modifications and combinations of the disclosed features are possible without departing from the scope of the following claims.

What is claimed is:

1. A computer-implemented method utilizing blockchain technology for managing healthcare records, the computer-implemented method comprising:
   providing a computer network with one or more computing devices that are interconnected through the computer network;
   managing identities and access permissions within the computer network through a Membership Service Provider (MSP) and a Certificate Authority (CA), wherein the MSP manages digital identities and authenticates member entities that are authorized to participate in the computer network, and the CA issues and manages digital certificates to ensure secure transactions and communications among the one or more computing devices;
   submitting a proposal related to a healthcare record from a first computing device of the one or more computing devices to a plurality of endorsing peers for approval, each of the endorsing peers comprising at least one computing device;
   approving the proposal by the plurality of endorsing peers with the at least one computing device and replying to the proposal with a response comprising a peer approved transaction;
   creating a spontaneous private peer-to-peer communication channel between the first computing device and a second computing device and transmitting data related to the healthcare record from the first computing device to the second computing device through the private peer-to-peer communication channel; and
   creating a block of transactions based on the data transmitted from the first computing device to the second computing device and adding the block of transactions to a ledger; and
   providing one or more Fast Healthcare Interoperability Resources (FHIR) Health Level 7 (HL7) tools to assist member organizations in the transformation of non-standard healthcare data into HL7 compliant formats, comprising:
   (a) an HL7 field mapper to align existing data field types with corresponding HL7 field types through a user interface;
   (b) a profile form template builder enabling members to create form templates by incorporating their HL7 mapped fields in an ad hoc manner; and (c) a profile form renderer to render forms based on user-defined templates, facilitating the submission of data network peers.

2. The computer-implemented method of claim 1, wherein creating the spontaneous private peer-to-peer communication channel between the first computing device and the second computing device, secured by leveraging digital certificates issued by the Certificate Authority (CA) and managed by the Membership Service Provider (MSP) ensuring that only authorized devices can establish such connections, comprises storing the data in a private state database on peers of authorized organizations and the data is accessible in the private state database from a chaincode.

3. The computer-implemented method of claim 2, wherein the creating the block of transactions comprises creating a hash value of the data and writing the hash value on a ledger of each of the peers of authorized organizations, wherein the ledger stores entries of the healthcare records that are invoked by the one or more computing devices.

4. The computer-implemented method of claim 3, wherein the ledger comprises a first smart contract that is assigned to a first peer on the first computing device and a second smart contract that is assigned to a second peer on the second computing device.

5. The computer-implemented method of claim 4, wherein the spontaneous private peer-to-peer communication channel is created after one or more of the first smart contract or the second smart contract are approved by the plurality of endorsing peers.

6. The computer-implemented method of claim 1, wherein the creating the spontaneous private peer-to-peer communication channel, secured by leveraging digital certificates issued by the Certificate Authority (CA) and managed by the Membership Service Provider (MSP) ensuring that only authorized devices can establish such connections, comprises using a communication channel to exchange information to allow a connection over a secured API, facilitated through the generation and use of unique short-lived API access tokens.

7. The computer-implemented method of claim 1, wherein the HL7 field mapper comprises functionality for creating custom field types when no equivalent HL7 field type exists, with a provision that all custom field types are reviewable by system administrators to ensure uniqueness and compliance with HL7 FHIR custom field specifications.

8. A computing system utilizing blockchain technology for managing healthcare records, the computing system comprising:
one or more processors; and
one or more computing devices comprising instructions that, when executed by the one or more processors, are configured to perform operations comprising:
providing a scalable computer network with the one or more computing devices that are interconnected through the computer network;
employing a Membership Service Provider (MSP) and a Certificate Authority (CA) within the computing system to manage and authenticate digital identities of participating entities, ensuring that each transaction and data exchange is securely conducted between verified computing devices and authorized users;
submitting a proposal related to a healthcare record from a first computing device of the one or more computing devices to a plurality of endorsing peers for approval, each of the endorsing peers comprising at least one computing device;
approving the proposal by the plurality of endorsing peers with the at least one computing device and replying to the proposal with a response comprising a peer approved transaction;
creating a spontaneous private peer-to-peer communication channel between the first computing device and a second computing device and transmitting data related to the healthcare record from the first computing device to the second computing device through the private peer-to-peer communication channel; and
creating a block of transactions based on the data transmitted from the first computing device to the second computing device and adding the block of transactions to a ledger; and
wherein the computing system is configured to support the integration of a plurality of Fast Healthcare Interoperability Resources (FHIR) Health Level 7 (HL7) tools to facilitate the conversion of data into the HL7 standard, further comprising:
organizations in converting their data into the HL7 standard, comprising:
a) an HL7 field mapper to align existing data field types with corresponding HL7 field types through a user interface;
b) a profile form template builder enabling members to create form templates by incorporating their HL7 mapped fields in an ad hoc manner; and
c) a profile form renderer to render forms based on user-defined templates, facilitating the submission of data network peers.

9. The computing system of claim 8, wherein creating the private peer-to-peer communication channel between the first computing device and the second computing device, secured by leveraging digital certificates issued by the Certificate Authority (CA) and managed by the Membership Service Provider (MSP) ensuring that only authorized devices can establish such connections, comprises storing the data in a private state database on peers of authorized organizations and the data is accessible in the private state database from a chaincode.

10. The computing system of claim 9, wherein the creating the block of transactions comprises creating a hash value of the data and writing the hash value on a ledger of each of the peers of authorized organizations, wherein the ledger stores entries of the healthcare records that are invoked by the one or more computing devices.

11. The computing system of claim 10, wherein the ledger comprises a first smart contract that is assigned to a first peer on the first computing device and a second smart contract that is assigned to a second peer on the second computing device.

12. The computing system of claim 11, wherein the private peer-to-peer communication channel is created after one or more of the first smart contract or the second smart contract are approved by the plurality of endorsing peers.

13. The computing system of claim 8, wherein the first computing device comprises a display that is configured to display information related to the healthcare record.

14. The computing system of claim 8, wherein the creating the private peer-to-peer communication channel comprises using a communication channel to exchange information to allow a connection over a secured API to be formed to exchange the data.

15. The computing system of claim 8, wherein the computing system is further configured to support the HL7 field mapper functionality of creating custom field types when no equivalent HL7 field type exists, with a provision that all custom field types can be reviewed by system administrators to ensure uniqueness and compliance with HL7 FHIR custom field specifications.

16. A computer-implemented method utilizing blockchain technology for managing healthcare records, the computer-implemented method comprising:
  providing a computer network with one or more computing devices that are interconnected through the computer network;
  managing identities and access permissions within the computer network through a Membership Service Provider (MSP) and a Certificate Authority (CA), wherein the MSP manages digital identities and authenticates member entities that are authorized to participate in the computer network, and the CA issues and manages digital certificates to ensure secure transactions and communications among the one or more computing devices;
  submitting a proposal related to a healthcare record from a first computing device of the one or more computing devices to a plurality of endorsing peers for approval, each of the endorsing peers comprising at least one computing device;
  approving the proposal by the plurality of endorsing peers with the at least one computing device and replying to the proposal with a response comprising a peer approved transaction;
  creating a spontaneous private peer-to-peer communication channel between the first computing device and a second computing device and transmitting data related to the healthcare record from the first computing device to the second computing device through the private peer-to-peer communication channel;
  creating a block of transactions based on the data transmitted from the first computing device to the second computing device and adding the block of transactions to a ledger; and
  providing oracle nodes and an Oracle builder system, for verifying data integrity and compliance within the computer network, and creating customizable oracle builds based on specific user-defined oracle functionality.

17. A computing system utilizing blockchain technology for managing healthcare records, the computing system comprising:
  one or more processors; and
  one or more computing devices comprising instructions that, when executed by the one or more processors, are configured to perform operations comprising:
    providing a scalable computer network with the one or more computing devices that are interconnected through the computer network;
    employing a Membership Service Provider (MSP) and a Certificate Authority (CA) within the computing system to manage and authenticate digital identities of participating entities, ensuring that each transaction and data exchange is securely conducted between verified computing devices and authorized users;
    submitting a proposal related to a healthcare record from a first computing device of the one or more computing devices to a plurality of endorsing peers for approval, each of the endorsing peers comprising at least one computing device;
    approving the proposal by the plurality of endorsing peers with the at least one computing device and replying to the proposal with a response comprising a peer approved transaction;
    creating a spontaneous private peer-to-peer communication channel between the first computing device and a second computing device and transmitting data related to the healthcare record from the first computing device to the second computing device through the private peer-to-peer communication channel; and
    creating a block of transactions based on the data transmitted from the first computing device to the second computing device and adding the block of transactions to a ledger;
  wherein the computing system is further configured to support oracle nodes and an "Oracle Builder" system, for verifying data integrity and compliance within the computer network, and creating customizable oracle builds based on specific user-defined oracle functionality.

* * * * *